(12) United States Patent
Bublitz et al.

(10) Patent No.: US 6,706,761 B1
(45) Date of Patent: Mar. 16, 2004

(54) DYED COMPOSITIONS CONTAINING INSECTICIDES

(75) Inventors: Mike-Dirk Bublitz, Burscheid (DE); Dietmar Kisters, Krefeld (DE); Rainer Hamprecht, Odenthal (DE)

(73) Assignee: S. C. Johnson & Son, Inc., Racine, WI (US)

( * ) Notice: Subject to any disclaimer, the term of this patent is extended or adjusted under 35 U.S.C. 154(b) by 0 days.

(21) Appl. No.: 10/031,870

(22) PCT Filed: May 3, 2000

(86) PCT No.: PCT/EP00/03946

§ 371 (c)(1), (2), (4) Date: Nov. 13, 2001

(87) PCT Pub. No.: WO00/69260

PCT Pub. Date: Nov. 23, 2000

(30) Foreign Application Priority Data

May 14, 1999 (DE) .......................................... 199 22 406

(51) Int. Cl.[7] ........................ A01N 53/00; A01N 53/10
(52) U.S. Cl. ...................... 514/531; 424/405; 424/406; 424/409; 514/609; 514/625; 514/645; 523/122
(58) Field of Search .................... 523/122; 514/531, 514/609, 625, 648; 424/405, 406, 409

(56) References Cited

U.S. PATENT DOCUMENTS

| | | | |
|---|---|---|---|
| 3,978,040 A | | 8/1976 | Gottschlich et al. |
| 4,045,430 A | * | 8/1977 | Hamprecht .................. 260/208 |
| 4,315,857 A | | 2/1982 | Buecheler |
| 4,550,676 A | | 11/1985 | Francis |
| 4,582,509 A | | 4/1986 | Buhler et al. |
| 4,824,827 A | | 4/1989 | Kelly et al. |
| 4,889,872 A | | 12/1989 | Naumann et al. |
| 4,952,401 A | | 8/1990 | Hobbs |
| 5,707,638 A | * | 1/1998 | Losel et al. .................. 424/407 |
| 6,296,865 B1 | * | 10/2001 | Dujardin et al. ............. 424/409 |
| 2002/0136748 A1 | | 9/2002 | Bublitz et al. |

FOREIGN PATENT DOCUMENTS

| | | |
|---|---|---|
| EP | 279 325 A2 | 2/1988 |
| EP | 02290592 | 11/1990 |
| EP | 567 018 A2 | 10/1993 |
| EP | 200292563 | 10/2000 |
| GB | 1308951 * | 3/1973 |
| JP | HEI 7-324003 | 12/1995 |
| WO | WO 97/29634 | 8/1997 |
| WO | WO 99/01030 | 1/1999 |

* cited by examiner

*Primary Examiner*—Neil S. Levy

(57) ABSTRACT

The invention relates to insecticide-comprising polymer-based compositions which, in order to recognize the point in time when the insecticide is exhausted, comprise at least one dye which, after the insecticide has evaporated, turns a different colour.

10 Claims, No Drawings

DYED COMPOSITIONS CONTAINING INSECTICIDES

This application is a §371 application claiming priority based on PCT/EP00/03946 which was filed on May 3, 2000, which in turn claims priority based on German Application No. 199 22406.4 which was filed on May 14, 1999.

The invention relates to insecticide-comprising polymer-based compositions which, in order to recognize the point in time when the insecticide is exhausted, comprise at least one dye which, after the insecticide has evaporated, turns a different colour.

WO 97/29 634 and 99/01 030 disclose insecticidal polymer-based compositions which release the active ingredient at elevated temperature and which can be processed to shaped articles (so-called vapour-producing tablets). The insecticides can be evaporated with the aid of heating devices; the application of the insecticides can thus be controlled as desired.

Dyes which indicate the depletion of the carrier of active ingredient by changing their colour have already been proposed for cellulose-based (cardboard) vapour-producing tablets. This type of dye is unsuitable for polymer-based insecticidal compositions.

One of the requirements which a dye for polymer-based insecticidal compositions must meet is that they must be capable of being distributed homogeneously in the polymer.

A further requirement which such a dye must meet is that no disadvantageous inter-actions with the insecticide result. One of the preferred insecticides of WO 97/29 634 and 99/01 030 is transfluthrin=(2,3,5,6-tetrafluorophenyl)-methyl (1R)-trans-3-(2,2-dichloroethenyl)-2,2-dimethylcyclopropanecarboxylate. Thus, the dye to be used in accordance with the invention should be compatible, in particular, with transfluthrin and indicate the exhaustion of the latter by a colour change. Moreover, this colour change should be drastic so that it is easy to notice.

It has now been found that o-cyanoazo dyes which comprise the unit (I)

$O_2N$—⟨benzene ring with X, Y⟩—N=N—

(X, Y = CN, NO₂)

are outstandingly suitable for this purpose.

The invention relates to dye-comprising polymer-based insecticidal compositions, characterized in that the dye comprises at least one compound of the formula

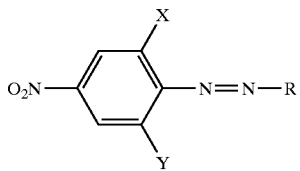

(II)

in which
  X, Y independently of one another represent CN or $NO_2$ and
  R represents an optionally substituted aromatic radical (with the proviso that X=Y=$NO_2$ must not apply).

The most important insecticides for the compositions according to the invention are pyrethroids.

The preferred pyrethroid active substances are:
1) 3-allyl-2-methyl-cyclopent-2-en-4-on-1-yl d/l-cis/trans-chrysanthemate (allethrin/Pynamin®),
2) 3-allyl-2-methyl-cyclopent-2-en-4-on-1-yl d-cis/trans-chrysanthemate (Pynamin forte®),
3) 3-allyl-2-methyl-cyclopent-2-en-4-on-1-yl d-trans-chrysanthemate (Bioallethrin®),
4) 2,3,5,6-tetrafluorobenzyl (+)-1R-trans-2,2-dimethyl-3-(2,2-dichlorovinyl)-cyclopropanecarboxylate (transfluthrin, Bayothrin®),
5) (S)-3-propargyl-2-methyl-cyclopent-2-en-4-on-1-yl (1R)-cis/trans-chrysanthemate (prallethrin/Etoc®),
or mixtures of these active substances.

Active substances which are particularly preferably used are 3-allyl-2-methyl-cyclopent-2-en-4-on-1-yl d-cis/trans-chrysanthemate (Pynamin forte®) and 2,3,5,6-tetrafluorobenzyl (+)-1R-trans-2,2-dimethyl-3-(2,2-dichlorovinyl)-cyclopropanecarboxylate(transfluthrin).

The polymer base on which the compositions according to the invention are based comprises at least one polymer with a softening range between 100 and 300° C., preferably between 150 and 250° C., in particular between 150 and 200° C.

In amorphous thermoplastic polymers, the softening range is identified by the glass transition temperature, and in semicrystalline polymers by the melting temperature.

Polymeric materials which are preferably used are amorphous and semicrystalline polymers and mixtures of these which can be processed thermoplastically, that is to say as a viscous melt, and whose softening range is below the boiling point of the active substances to be incorporated under atmospheric pressure. The polymers for the active substance in question are chosen in such a way that the active substance mixes with the polymer at least to some extent.

Suitable polymers which are preferably used are:

PVC (non-rigid), polystyrene, styrenetbutadiene, styrene/acrylonitrile, acrylonitrile/butadiene/styrene, polymethyl acrylate, amorphous polycycloolefins, cellulose esters, aromatic polycarbonates, amorphous aromatic polyamides, polyphenylene ethers, poly(ether) sulphones, polyimides, polyethylene, polypropylene, polybutylene, polymethylpentene, PVC (rigid), polyamide, polyether amides, polyester amides, polyoxymethylene, polyethylene terephthalate, polybutylene terephthalate, polyimide, polyether (ether) ketone and polyurethanes.

Examples of preferred mixtures are:

blends of polycarbonates with polybutylene terephthalate, blends of polyamide-6 and styrene/acrylonitrile, blends of polypropylene and polymethylpentene.

Particularly preferred are polypropylene, poly-4-methyl-1-pentene and mixtures of these.

The compositions according to the invention are preferably based on mixtures comprising A. 0.1 to 80% by weight, preferably 0.2 to 40% by weight, in particular 0.5 to 20% by weight, specifically 1 to 12% by weight of transfluthrin

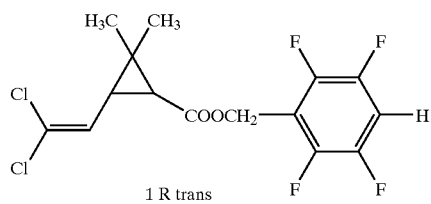

(III)

and

B. 99.9 to 20% by weight, preferably 99.8 to 60% by weight, in particular 99.5 to 80% by weight, specifically 99 to 88% by weight of poly-4-methyl-1-pentene which, in turn, can be replaced by another poly-α-olefin to up to half, preferably up to a third, in particular up to a quarter of its weight, the percentages in each case relating to the total of components A+B.

Transfluthrin and a process for its preparation are disclosed in German Offenlegungsschrift 37 05 224 (=European Patent Specification 279 325).

Poly-4-methyl-1-pentene B is a polymer, preferably with a glass transition temperature of 50 to 60° C., a softening temperature measured by the Vicat method (ASTM D 1525) of 140 to 180° C., preferably 170 to 175° C., and a melt-flow index (260° C./5 kg), measured in accordance with ASTM D 1238, of 20 to 200, preferably 22 to 35[g/10 min]; it is known that it can be prepared by polymerizing 4-methyl-1-pentene Suitable poly-α-olefins which can replace some of the poly-4-methyl-1-pentene are mainly polyethylenes, polypropylenes, polybutenes and polyisobutenes and copolymers of the α-olefins on which the abovementioned polymers are based, such as, for example, ethylene/propylene copolymers. Preferred polypropylenes comprise iso- and/or syndiotactic polypropylenes, preferably with a softening temperature, measured by the Vicat method (ISO 306), of 130 to 170° C., preferably 140 to 160° C., and a melt-flow index (230° C./2 kg), measured in accordance with ISO 1133, of 20 to 40, preferably 25 to 35 [g/10 min].

In the event that "other" poly-α-olefins are concomitantly used, the weight ratio of poly-4-methyl-1-pentene/poly-α-olefins can be 70:30 to 99:1, preferably 80:20 to 95:5.

Radicals R which are suitable for the compounds of the formula (II) are radicals of coupling components of the benzene, naphthalene, indole, pyridine and tetrahydroquinoline series, but preferably N-substituted paminoaryl radicals and, in particular, anilines of the formula

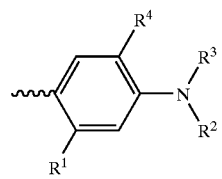

(IV).

In this formula, $R^1$ represents hydrogen, $C_1$–$C_{18}$-alkyl, $C_1$–$C_{18}$-alkoxy, $C_6$–$C_{16}$-aryloxy, $C_1$–$C_{12}$-alkylcarbonylamino, $C_6$–$C_{12}$—Ar—$C_1$–$C_4$-alkylcarbonylamino, $C_5$–$C_{12}$-cycloalkylcarbonylamino, $C_6$–$C_{15}$-arylcarbonyl amino, $C_1$–$C_5$-heteroylcarbonylamino, $C_1$–$C_{12}$-alkoxycarbonylamino, $C_1$–$C_{12}$-alkylsulphonylamino, $C_6$–$C_{15}$-arylsulphonylamino, aminocarbonylamino, CN, $CF_3$, carbamoyl, di-$C_1$–$C_6$-alkylaminocarbonyl, $C_1$–$C_{12}$-alkoxycarbonyl, sulphamoyl, di-$C_1$–$C_6$-alkylaminosulphonyl or $C_1$–$C_{12}$-alkylsulphonyl, $R^2$ represents hydrogen, $C_1$–$C_{18}$-alkyl, $C_6$–$C_{12}$—Ar—$C_1$–$C_4$-alkyl or $C_6$–$C_5$-aryl, $R^3$ represents hydrogen, $C_1$–$C_{18}$-alkyl or $C_6$–$C_{12}$—Ar—$C_1$–$C_4$-alkyl, and $R^4$ represents hydrogen, $C_1$–$C_{18}$-alkyl, $C_1$–$C_{18}$-alkoxy, $C_5$–$C_{15}$-aryloxy, $C_6$–$C_{12}$—Ar—$C_1$–$C_4$-alkoxy, halogen, CN, carboxyl or $C_1$–$C_{12}$-alkoxycarbonyl.

The alkyl and alkoxy radicals mentioned above in any desired context (that is to say also, for example, alkylsulphonyl or alkoxycarbonyl) are preferably to be understood as radicals having 1 to 4 C atoms which are preferably monosubstituted by OH, CN, halogen, $C_1$–$C_4$-alkoxy, $C_2$–$C_5$-alkylcarbonyloxy or by ammonium groups of the formula

(V)

where $Q_1$, $Q_2$ and $Q_3$ represent $C_1$–$C_6$-alkyl, $C_5$–$C_{12}$-cycloalkyl, $C_6$—Ar—$C_1$–$C_4$-alkyl or $C_6$-aryl or else form the remaining members of an N-heterocycle such as pyridine, imidazole and triazole, while the aryl or aryloxy radicals are preferably understood as meaning phenyl or phenoxy radicals which are optionally monosubstituted by Cl, Br, $NO_2$, CN, $C_1$–$C_4$-alkoxy or $C_1$–$C_4$-alkyl.

Very particular preference is given to a dye of the formula

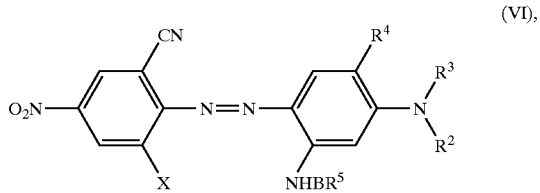

(VI), in which

B represents —CO—, —$CO_2$— or —$SO_2$—, $R^5$ represents $C_1$–$C_6$-alkyl, $C_6$—Ar—$C_1$–$C_4$-alkyl, $C_6$-aryl or $NV^1V^2$, $V^1$ represents hydrogen, $C_1$–$C_{18}$-alkyl, $C_6$—Ar—$C_1$–$C_4$-alkyl or $C_6$–$C_{12}$-aryl, $V^2$ represents hydrogen, $C_1$–$C_{18}$-alkyl or $C_6$—Ar—$C_1$–$C_4$-alkyl, $R^2$ represents hydrogen, $C_1$–$C_{18}$-alkyl, $C_6$—Ar—$C_1$–$C_4$-alkyl or $C_6$–$C_{12}$-aryl, $R^3$ represents hydrogen, $C_1$–$C_{18}$-alkyl or $C_6$—Ar—$C_1$–$C_4$-alkyl and $R^4$ represents hydrogen, $C_1$–$C_{18}$-alkyl, $C_1$–$C_{18}$-alkoxy, $C_6$–$C_{12}$-aryloxy or $C_6$—Ar—$C_1$–$C_4$-alkoxy and, preferably, with the proviso that, if $R^5=NV^1V^2$, then B=—CO— or —SO$_2$—.

Again, the alkyl and alkoxy radicals are preferably understood as meaning those radicals which have 1 to 4 C atoms which are preferably monosubstituted by OH, CN, halogen, $C_1$–$C_4$-alkoxy or $C_2$–$C_5$-alkylcarbonyloxy, while the aryl or aryloxy radicals are preferably understood as meaning phenyl or phenoxy radicals which are optionally monosubstituted by Cl, Br, NO$_2$, CN, $C_1$–$C_4$-alkoxy or $C_1$–$C_4$-alkyl.

It is preferred for the dye for the compositions according to the invention to have the formula

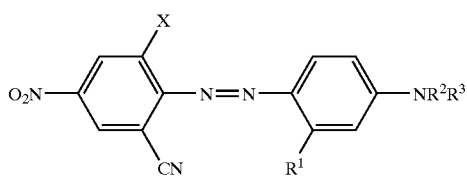

(VII), in which

X represents cyano or nitro, $R^2$ represents straight-chain or branched $C_1$–$C_{10}$-alkyl, optionally substituted by halogen, OH, acyloxy, CN or phenyl which, in turn, can be substituted by $C_1$–$C_4$-alkyl or halogen, $R^3$ represents H and the meanings given for $R^2$ and $R^1$ represents H, $C_1$–$C_4$-alkyl, $C_1$–$C_8$-acylamino or $C_1$–$C_4$-alkylsulphonylamino.

Preference is given to such a dye of the formula (VII) in which $R^1$ represents methyl or acetamino.

An especially preferred dye for the compositions according to the invention has one of the following formulae:

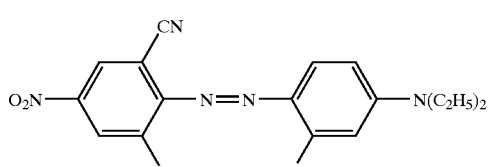

(VIII)

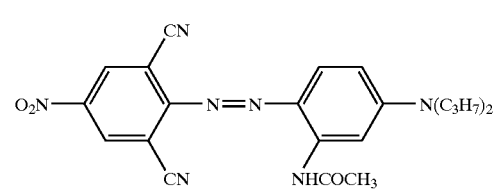

(IX)

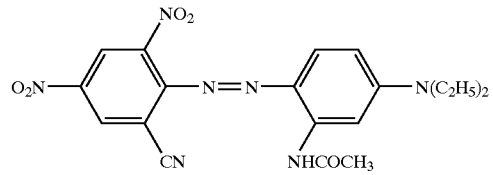

(X)

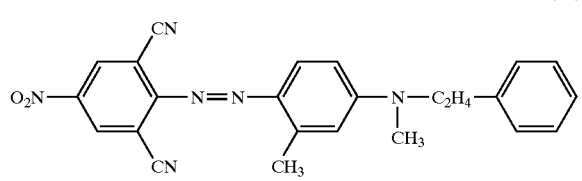

(XI)

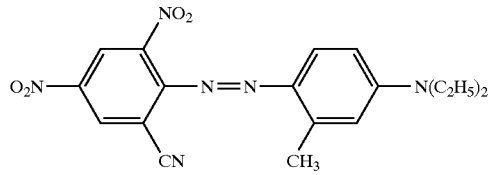

(XII)

The dyes of the formula (II) and processes for their preparation are known; cf. for example, German Offenlegungsschrift 24 56 495.

Most the dyes to be used in accordance with the invention dye the insecticidal polymer compositions a reddish-blue to blue. The fact that the colour change to colourless is noticed easily is a particular advantage of the invention.

The compositions according to the invention comprise 0.001 to 0.5% by weight, preferably 0.006 to 0.15% by weight, in particular 0.024 to 0.11% by weight of dye (II) based on the total of insecticide and polymer.

The compositions according to the invention generally comprise between 0.1 and 80% by weight, preferably between 0.2 and 40% by weight, particularly preferably between 1.0 and 20% by weight of insecticide, based on the total of insecticide and polymer.

Additives which can be used are modifiers and/or fillers and reinforcing agents and/or processing auxiliaries such as, for example, nucleating agents, plasticizers, release agents, flame retardants, impact resistance modifiers, stabilizers or other additives conventionally used in the thermoplast field. Fillers which are preferably used are those described in the Encyclopedia of Polymer Science and Engineering, Vol. 7, pp. 53–73 (1985).

Fillers and reinforcing agents which can be used are minerals such as, for example, gypsum, lime, glass fibres, sand, titanium(IV) oxide, preferably glass fibres.

The amount of the additives may vary within wide limits; in general, it is 1 to 80% by weight, preferably 0.2 to 50% by weight, in particular 0.5 to 30% by weight, based on additive-comprising composition according to the invention.

The compositions according to the invention can be prepared by introducing the polymer into a suitable kneader or extruder in the form of pellets or a powder, and plastifying it. Insecticide and dye can be directly introduced, under the plastifyng conditions and temperatures which are typical for the polymer, into the polymer melt via a suitable metering device and distributed uniformly therein.

The active-substance-comprising polymers can be pelleted in various ways. For example, either extruded and fully or partly cooled extrudates are cut (extrudate pelletization), or else the hot melt is subjected to die-head pelletization (for example water-cooled die-face pelletization).

The resulting insecticide-comprising granules can be processed thermoplastically to give shaped articles or processed together with other polymers to give blends (master batch).

Shaping methods which can be used are those conventionally used in polymers, such as, for example, injection moulding, extrusion blow-moulding, film extrusion or thermo-forming.

The compositions according to the invention can be used in the form of vapour-releasing tablets in conventional vaporizers as they are employed, for example, for vapour-releasing tablets made of cellulose. Working temperatures from 60 to 180° C., preferably 130 to 170° C., ensure a relatively uniform long-term release of active substance into the environment.

The invention furthermore relates to the use of the compositions according to the invention for controlling insects such as, for example, flies and midges.

In the examples which follow, the percentages are always by weight.

EXAMPLES

Example 1

Preparation of the Polymer/Active Substance Pellets 1.1 Extrusion conditions:
  Extruder: Brabender PL 2000 twin-screw extruder (35/17D), screw type S
  Conditions: Temperature 280/280/270/280° C.,—100 rpm—6 kg/h
  Screw flight content: approx. 250 g
1.2 Preparations:
  A. In a 5 plastic container, homogenize polymer TPX RT 18 (see Example 3) and dye in an Engelmann's gyro mixer, type Elte 650 (3 kg/tank)
  B. Dissolve the BHT (=butylhydroxytoluene) in the warm transfluthrin (approx. 50° C.) and then filter the solution through a G4 glass frit.
1.3 Metering:
  TPX RT 18 and dye are metered into the extruder using an Engelhardt type 150 proportioning weigher and transfluthrin/BHT are metered into the extruder using an Ismatec type MV-Z gear pump (pipe heated with slow steam), all at the same time.
1.4 Pelletization:
  The extrudate is extruded into a water bath (length 2.5 m), predried over a water extraction section (in-house construction) and pelletized using a Scheer type SGS 50-E pelletizer. The starting loss is approx. 300 g.

Example 2

Injection Moulding

Blend: 100% active substance pellets
2.1 Conditions for injection moulding
  Machine: Arburg 320-210-850, single screw Ø35 mm, screw flight content approx. 125 g (corresponds to 5 shots)
  Temperature profile: 250° C. (nozzle)/265° C./270° C./280° C. (inverse temperature profile)
  Cycle time: 15 seconds
  Mould temperature: 30° C.
  Mould: Cold runner, 12-cavity mould, injection via tunnel gate
  Drying of the product: approx. 15 hours at 50° C. in a vacuum drying oven
  Pre-run 10 shots at 25 g each
  Sprue recycling: an admixture of 10–15% is possible.
  Dimensions of the vapour-releasing polymer tablets: 34 mm×22 mm×2.5 mm.

Example 3

Composition of the Polymer Tablets With Dyes

The following vapour-releasing polymer tablets were prepared by the abovementioned method.

| Example | Position | Quantity (%) |
| --- | --- | --- |
| 3.1 | TPX* | 91.261 |
|  | transfluthrin (Al$_2$O$_3$ washed) | 8.300 |
|  | BHT** | 0.415 |
|  | Dye XII | 0.024 |
| 3.2 | TPX* | 91.261 |
|  | transfluthrin (Al$_2$O$_3$ washed) | 8.300 |
|  | BHT** | 0.415 |
|  | Dye XII | 0.024 |
| 3.3 | TPX* | 91.255 |
|  | transfluthrin (Al$_2$O$_3$ washed) | 8.300 |
|  | BHT** | 0.415 |
|  | Dye XII | 0.030 |
| 3.4 | TPX | 91.040 |
|  | transfluthrin | 8.300 |
|  | BHT | 0.415 |
|  | titanium dioxide (®Bayertitan R-FK-2) | 0.200 |
|  | Dye XII | 0.040 |
| 3.5 | TPX | 91.245 |
|  | transfluthrin | 8.300 |
|  | BHT | 0.415 |
|  | Dye XII | 0.040 |

*TPX = poly-4-methyl-1-pentene by Mitsui (polymethylpentene TPX RT 18)
**BHT = butylhydroxytoluene

Example 4

Testing the Colour Changes

The method below describes the testing of the end-point indication (colour change) of vapour-releasing polymer tablets by visually assessing the colour change of the tablets.

At least three 3 test tablets are used per experiment. The test tablets are inserted into the heating devices in such a way that they lie in the middle on the heating block of the device in question. Then, the heating devices together with the test tablets are plugged into the multiple socket units while switched off.

The timers are set for the defined test period.

Amongst the possible test period models
  a. 8 hours evaporation time/day 1 cycle
  b. 24 hours evaporation time/day 3 cycles,
model a was preferably used.

After each of the defined evaporation times had elapsed, all tablets, were removed from the heating devices and checked visually for any colour change with reference to an untreated sample.

The end-point indication is ensured when the colouring of the test product used differs clearly from that of the as yet unused product, for example:

change from dark blue to amber.
unambiguous fading of the test product.

| Example | Composition No. | Assessment |
|---------|-----------------|------------|
| 4.1 | 3.1 | ++ |
| 4.2 | 3.2 | ++ |
| 4.3 | 3.3 | + |
| 4.5 | 3.5 | ++ |

+ Discoloration clearly visible
++ Discoloration very clearly visible

What is claimed is:

1. A composition comprising a pyrethroid insecticide, a polymer and at least one dye compound of the formula

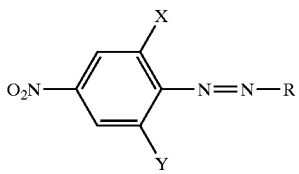

(II)

in which X, Y independently of one another represent CN or $NO_2$ and R represents an optionally substituted aromatic radical, with the proviso that $X=Y=NO_2$ must not apply.

2. The composition according to claim 1 where R in formula (II) represents

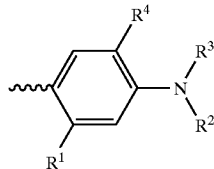

(IV)

in which $R^1$ represents hydrogen, $C_1$–$C_{18}$-alkyl, $C_1$–$C_{18}$-alkoxy, $C_6$–$C_{16}$-aryloxy, $C_1$–$C_{12}$-alkylcarbonylamino, $C_6$–$C_{12}$—Ar—$C_1$–$C_4$-alkylcarbonylamino, $C_5$–$C_{12}$-cycloalkylcarbonylamino, $C_6$–$C_{15}$-arylcarbonylamino, $C_1$–$C_5$-heteroylcarbonylamino, $C_1$–$C_{12}$-alkoxycarbonylamino, $C_1$–$C_{12}$-alkylsulphonylamino, $C_6$–$C_{15}$-arylsulphonylamino, aminocarbonylamino, CN, $CF_3$, carbamoyl, di-$C_1$–$C_6$-alklaminocarbonyl, $C_1$–$C_{12}$-alkoxycarbonyl, sulphamoyl, di-$C_1$–$C_6$alkylaminosulphonyl or $C_1$–$C_{12}$-alkylsulphonyl, $R^2$ represents hydrogen, $C_1$–$C_{18}$-alkyl, $C_6$–$C_{12}$—Ar—$C_1$–$C_4$-alkyl or $C_6$–$C_{15}$-aryl, $R^3$ represents hydrogen, $C_1$–$C_{18}$-alkyl or $C_6$–$C_{12}$—Ar—$C_1$–$C_4$-alkyl, and $R^4$ represents hydrogen, $C_1$–$C_{18}$-alkyl, $C_1$–$C_8$-alkoxy, $C_5$–$C_{15}$-aryloxy, $C_6$–$C_{12}$—Ar—$C_1$–$C_4$-alkoxy, halogen, CN, carboxyl or $C_1$–$C_{12}$-alkoxycarbonyl.

3. The composition according to claim 1, in which the dye compound is of the formula

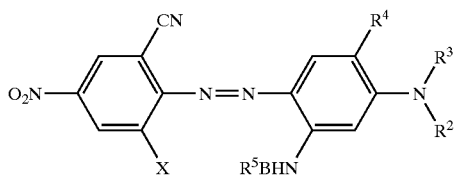

(VI)

, in which

B represents —CO—, —$CO_2$— or —$SO_2$—, $R^5$ represents $C_1$–$C_6$-alkyl, $C_6$—Ar—$C_1$–$C_4$-alkyl, $C_6$-aryl or $NV^1V^2$, $V^1$ represents hydrogen, $C_1$–$C_{18}$-alkyl, $C_6$–$C_{12}$—Ar—$C_1$–$C_4$-alkyl or $C_6$–$C_{12}$-aryl, $V^2$ represents hydrogen, $C_1$–$C_{18}$-alkyl or $C_6$–$C_{12}$—Ar—$C_1$–$C_4$-alkyl, $R^2$ represents hydrogen, $C_1$–$C_{18}$-alkyl, $C_6$–$C_{12}$—Ar—$C_1$–$C_4$-alkyl or $C_6$–$C_{12}$-aryl, $R^3$ represents hydrogen, $C_1$–$C_{18}$-alkyl or $C_6$–$C_{12}$—Ar—$C_1$–$C_4$-alkyl and $R^4$ represents hydrogen, $C_1$–$C_8$-alkyl, $C_1$–$C_{18}$-alkoxy, $C_6$–$C_{12}$-aryloxy or $C_6$—Ar—$C_1$–$C_4$-alkoxy and, preferably, with the proviso that, if $R^5=NV^1V^2$, then B=—CO— or —$SO_2$—.

4. The composition according to claim 1, in which the dye compound is of the formula

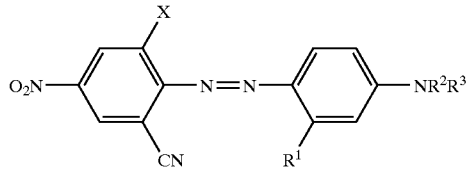

(VII)

, in which

X represents cyano or nitro, $R^2$ represents straight-chain or branched $C_1$–$C_{10}$-alkyl, optionally substituted by halogen, OH, acyloxy, CN or phenyl which, in turn, can be substituted by $C_1$–$C_4$-alkyl or halogen, $R^3$ represents H and the meanings given for $R^2$ and $R^1$ represents H, $C_1$–$C_4$-alkyl, $C_1$–$C_8$-acylamino or $C_1$–$C_4$-alkylsulphonylamino.

5. The composition according to claim 4, in which $R^2$ represents straight-chain $C_1$–$C_4$-alkyl or phenylpropyl, $R^3$ represents straight-chain $C_1$–$C_4$-alkyl and $R^1$ represents methyl or $C_1$–$C_4$-acylamino.

6. The composition according to claim 1, in which the insecticide is transfluthrin.

7. The composition according to claim 1, in which the polymer is polymethylpentene.

8. The composition according to claim 1 which comprises 0.001 to 0.5% by weight of dye of the formula (II), 0.1 to 80% by weight of insecticide and 1 to 80% by weight of polymer, in each case based on the total insecticide and polymer.

9. A method for controlling insects comprising the step of:
applying the composition of claim 1 to a target area to control insects in the area.

10. The composition of claim 1, wherein the composition has a bluish tint, and wherein upon heating the composition will change to a more colorless appearance as the insecticide vaporizes from the composition.

* * * * *